(12) United States Patent
Goldberg et al.

(10) Patent No.: US 6,821,751 B2
(45) Date of Patent: Nov. 23, 2004

(54) HYPOXIA RESPONSIVE TRANSCRIPTION ENHANCER ELEMENT FROM YEAST

(75) Inventors: Mark Alan Goldberg, Needham, MA (US); Michael Vasconcelles, Wellesley, MA (US); Yide Jiang, Newton, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 168 days.

(21) Appl. No.: 10/041,675

(22) Filed: Jan. 10, 2002

(65) Prior Publication Data

US 2003/0060439 A1 Mar. 27, 2003

Related U.S. Application Data

(60) Provisional application No. 60/260,678, filed on Jan. 11, 2001.

(51) Int. Cl.$^7$ .................. C12P 21/06; A01N 63/00; C12N 15/00; C12N 15/63; C07H 21/04

(52) U.S. Cl. .................. 435/69.1; 435/320.1; 435/455; 424/93.2; 424/93.4; 536/23.1; 536/24.1

(58) Field of Search .................. 536/23.1, 24.1; 435/325, 320.1, 455, 69.1; 424/93.21, 93.2

(56) References Cited

PUBLICATIONS

Morimyo et al., EST Accession No. AU014066, 1998, p. 6.*
Marra et al., EST Accession No. AA571090, 1997, p. 6–7.*
Draper, K., 1997, issued patent 5,610,054, p. 1 (computer printout).*
Velculescu et al., 2000, Geneseq Accession No. AAF40600, p. 1, 2.*
Ansell, et al., "The Two Isoenzymes for Yeast NAD$^+$–Dependent Glycerol 3–Phosphate Dehydrogenase Encoded by GPD1 and GPD2 Have Distinct Roles in Osmoadaptation and Redox Regulation," *Embo J.* 16:2179–2187 (1997).
Beck, et al., "Enhancer Element at the 3'–Flanking Region Controls Transcriptional Response to Hypoxia in the Human Erythropoietin Gene," *J. Biol. Chem.* 266:15563–15566 (1991).
Blanchard, et al., "Hypoxic Induction of the Human Erythropoietin Gene: Cooperation between the Promoter and Enhancer, Each of Which Contains Steroid Receptor Response Elements," *Mol. Cell. Biol.* 12:5373–5385 (1992).
Bourot, et al., "Isolation and Characterization of the *Saccharomyces cerevisiae* SUT1 Gene Involved in Sterol Uptake," *Gene* 165:97–102 (1995).
Bunn, et al., "Oxygen Sensing and Molecular Adaptation to Hypoxia," *Physiol. Rev.* 76:839–885 (1996).
Choi, et al., "Regulatory Elements that Control Transcription Activation and Unsaturated Fatty Acid–Mediated Repression of the *Saccharomyces cerevisiae* OLE1 Gene," *J. Biol. Chem.* 271:3581–3589 (1996).

Deckert, et al., "The Anatomy of a Hypoxic Operator in *Saccharomyces cerevisiae*," *Genetics* 150:1429–1441 (1998).
Donzeau, et al., "Regulation by Low Temperature and Anaerobiosis of a Yeast Gene Specifying a Putative GPI–Anchored Plasma Membrane," *Molec. Microbiol.* 20:449–459 (1996).
Ebert, et al., "Regulation of the Erythropoietin Gene," *Blood* 94:1864–1877 (1999).
Fujimori, et al., Isolatioin and Characterization of Mutations Affecting Expression of the Δ9–Fatty Acid Desaturase Gene, OLE1, in *Saccharomyces cerevisiae*, *FEBS Letters* 413:226–230 (1997).
Fujiwara, et al., "Molecular Mechanism of the Multiple Regulation of the *Saccharomyces cerevisiae* ATF1 Gene Encoding Alcohol Acetyltransferase," *Yeast* 15:1183–1197 (1999).
Goldberg, et al., "Regulation of the Erythropoietin Gene: Evidence that the Oxygen Sensor Is a Heme Protein," *Science* 242:1412–1415 (1988).
Hassett, et al., "Regulation of High Affinity Iron Uptake in the Yeast *Saccharomyces cerevisiae*," *J. Biol. Chem.* 273:7628–7636 (1998).
Horiguchi, et al., "Erythropoietin Induction in Hep3B Cells Is Not Affected by Inhibition of Heme Biosynthesis," *Biochim. Biophys. Acta* 1495:231–236 (2000).
Huang, et al., "Activation of Hypoxia–Inducible Transcription Factor Depends Primarily Upon Redox–Sensitive Stabilization of Its α Subunit," *J. Biol. Chem.* 271:32253–32259 (1996).
Huang, et al., "Inhibition of Hypoxia–Inducible Factor 1 Activation by Carbon Monoxide and Nitric Oxide," *J. Biol. Chem.* 274:9038–9044 (1999).
Kwast, et al., "Oxygen Sensing in Yeast: Evidence for the Involvement of the Respiratory Chain in Regulating the Transcription of a Subset of Hypoxic Genes," *Proc. Natl. Acad. Sci. USA* 96:5446–5451 (9999).
Kwast, et al., "Oxygen Sensing and the Transcriptional Regulation of Oxygen–Responsive Genes in Yeast," *J. Exper. Biol.* 201:1177–1195 (1998).
Levy, et al., "Transcriptional Regulation of the Rat Vascular Endothelial Growth Factor Gene by Hypoxia," *J. Biol. Chem.* 270:13333–13340 (1995).

(List continued on next page.)

*Primary Examiner*—Shin–Lin Chen
(74) *Attorney, Agent, or Firm*—Michael A. Sanzo; Fitch, Even, Tabin & Flannery

(57) ABSTRACT

The present invention is directed to DNA elements that enhance cellular gene expression in response to anaerobic growth or the presence of certain inducing agents. The enhancer element may be incorporated into expression vectors and used to increase the production of recombinant proteins.

21 Claims, 1 Drawing Sheet

U.S. PATENT DOCUMENTS

Poyton, "Models for Oxygen Sensing in Yeast: Implications for Oxygen–Regulated Gene Expression in Higher Eucaryotes," *Respir. Biol.* 115:119–133 (1999).

Rachidi, et al., "*Saccharomyces cerevisiae* PAU Genes Are Induced by Anaerobiosis," *Molec. Microbiol.* 35:1421–1430 (2000).

Semenza, et al., "A Nuclear Factor Induced by Hypoxia Via De Novo Protein Synthesis Binds to the Human Erythropoietin Gene Enhancer at a Site Required for Transcriptional Activation," *Molec. Cell. Biol.* 12:5447–5454 (1992).

Scott, et al., "Concerted Action of the Transcriptional Activators REB1, RAP1, and GCR1 in the High–Level Expression of the Glycolytic Gene TPI," *Molec. Cell. Biol.* 13:543–550 (1993.

Sertil, et al., "The DAN1 Gene of *S. cerevisiae* Is Regulated in Parallel with Hypoxic Genes, but by a Different Mechanism," *Gene* 192:199–205 (1997).

Stukey, et al., "The OLE1 Gene of *Saccharomyces cerevisiae* Encodes Δ9Fatty Acid Desaturase and Can Be Functionally Replaced by the Rat Stearoyl–CoA Desaturase Gene," *J. Biol. Chem.* 265:20144–20149 (1990).

Zitomer, et al., "Approaches to the study of Rox1 Repression of the Hypoxic Genes in the Yeast *Saccharomyces cerevisiae*," *Methods* 11:279–288 (1997).

Zitomer, et al., "Regulation of Gene Expression by Oxygen in *Saccharomyces cerevisiae*," *Microbiol. Rev.* 56:1–11 (1992).

* cited by examiner

| Mutation | -347           -328 | DNA binding |
|---|---|---|
| WT | GAACACTCAACAAACCTTAT | 100 |
| G347T | t------------------- | 122 |
| A346C | -c------------------ | 81 |
| A345C | --c----------------- | 110 |
| C344A | ---a---------------- | 118 |
| A343C | ----c--------------- | 80 |
| A343T | ----t--------------- | 51 |
| C342A | -----a-------------- | 10 |
| T341G | ------g------------- | 17 |
| T341C | ------c------------- | 48* |
| T341A | ------a------------- | 32 |
| C340A | -------a------------ | 5 |
| A339C | --------c----------- | 31 |
| A338C | ---------c---------- | 19 |
| C337A | ----------a--------- | 18 |
| C337T | ----------t--------- | 19 |
| A336C | -----------c-------- | 54* |
| A336T | -----------t-------- | 26 |
| A336G | -----------g-------- | 42* |
| A335C | ------------c------- | 53* |
| A334C | -------------c------ | 127 |
| C333A | --------------a----- | 228 |
| C332A | ---------------a---- | 98 |
| T331G | ----------------g--- | 138 |
| T330G | -----------------g-- | 129 |
| A329C | ------------------c- | 149 |
| T328G | -------------------g | 126 |

Figure 1

SEQUENCE LISTING

<160> NUMBER OF SEQ ID NOS: 61

<210> SEQ ID NO 1
<211> LENGTH: 9
<212> TYPE: DNA
<213> ORGANISM: Saccharomyces cerevisiae

<400> SEQUENCE: 1 acycaacaa                                                                    9

<210> SEQ ID NO 2
<211> LENGTH: 20
<212> TYPE: DNA
<213> ORGANISM: Saccharomyces cerevisiae

<400> SEQUENCE: 2
gaacacycaa caaaccttat                                                       20

<210> SEQ ID NO 3
<211> LENGTH: 20
<212> TYPE: DNA
<213> ORGANISM: Saccharomyces cerevisiae

<400> SEQUENCE: 3
gaacactcaa caaaccttat                                                       20

<210> SEQ ID NO 4
<211> LENGTH: 20
<212> TYPE: DNA
<213> ORGANISM: Saccharomyces cerevisiae

<400> SEQUENCE: 4
taacactcaa caaaccttat                                                       20

<210> SEQ ID NO 5
<211> LENGTH: 20
<212> TYPE: DNA

-continued

<213> ORGANISM: Saccharomyces cerevisiae

<400> SEQUENCE: 5
gcacactcaa caaaccttat                                        20

<210> SEQ ID NO 6
<211> LENGTH: 20
<212> TYPE: DNA
<213> ORGANISM: Saccharomyces cerevisiae

<400> SEQUENCE: 6
gaccactcaa caaaccttat                                        20

<210> SEQ ID NO 7
<211> LENGTH: 20
<212> TYPE: DNA
<213> ORGANISM: Saccharomyces cerevisiae

<400> SEQUENCE: 7
gaaaactcaa caaaccttat                                        20

<210> SEQ ID NO 8
<211> LENGTH: 20
<212> TYPE: DNA
<213> ORGANISM: Saccharomyces cerevisiae

<400> SEQUENCE: 8
gaaccctcaa caaaccttat                                        20

<210> SEQ ID NO 9
<211> LENGTH: 20
<212> TYPE: DNA
<213> ORGANISM: Saccharomyces cerevisiae

<400> SEQUENCE: 9
gaactctcaa caaaccttat                                        20

<210> SEQ ID NO 10
<211> LENGTH: 20
<212> TYPE: DNA
<213> ORGANISM: Saccharomyces cerevisiae

<400> SEQUENCE: 10
gaacaatcaa caaaccttat                                        20

<210> SEQ ID NO 11
<211> LENGTH: 20
<212> TYPE: DNA
<213> ORGANISM: Saccharomyces cerevisiae

<400> SEQUENCE: 11
gaacacgcaa caaaccttat                                        20

<210> SEQ ID NO 12
<211> LENGTH: 20
<212> TYPE: DNA
<213> ORGANISM: Saccharomyces cerevisiae

<400> SEQUENCE: 12
gaacacccaa caaaccttat                                        20

<210> SEQ ID NO 13
<211> LENGTH: 20

```
<212> TYPE: DNA
<213> ORGANISM: Saccharomyces cerevisiae

<400> SEQUENCE: 13
gaacacacaa caaaccttat                                              20

<210> SEQ ID NO 14
<211> LENGTH: 20
<212> TYPE: DNA
<213> ORGANISM: Saccharomyces cerevisiae

<400> SEQUENCE: 14
gaacactaaa caaaccttat                                              20

<210> SEQ ID NO 15
<211> LENGTH: 20
<212> TYPE: DNA
<213> ORGANISM: Saccharomyces cerevisiae

<400> SEQUENCE: 15
gaacactcca caaaccttat                                              20

<210> SEQ ID NO 16
<211> LENGTH: 20
<212> TYPE: DNA
<213> ORGANISM: Saccharomyces cerevisiae

<400> SEQUENCE: 16
gaacactcac caaaccttat                                              20

<210> SEQ ID NO 17
<211> LENGTH: 20
<212> TYPE: DNA
<213> ORGANISM: Saccharomyces cerevisiae

<400> SEQUENCE: 17
gaacactcaa aaaaccttat                                              20

<210> SEQ ID NO 18
<211> LENGTH: 20
<212> TYPE: DNA
<213> ORGANISM: Saccharomyces cerevisiae

<400> SEQUENCE: 18
gaacactcaa taaaccttat                                              20

<210> SEQ ID NO 19
<211> LENGTH: 20
<212> TYPE: DNA
<213> ORGANISM: Saccharomyces cerevisiae

<400> SEQUENCE: 19
gaacactcaa ccaaccttat                                              20

<210> SEQ ID NO 20
<211> LENGTH: 20
<212> TYPE: DNA
<213> ORGANISM: Saccharomyces cerevisiae

<400> SEQUENCE: 20
gaacactcaa ctaaccttat                                              20

<210> SEQ ID NO 21
```

-continued

<210> SEQ ID NO 21
<211> LENGTH: 20
<212> TYPE: DNA
<213> ORGANISM: Saccharomyces cerevisiae

<400> SEQUENCE: 21
gaacactcaa cgaaccttat                                               20

<210> SEQ ID NO 22
<211> LENGTH: 20
<212> TYPE: DNA
<213> ORGANISM: Saccharomyces cerevisiae

<400> SEQUENCE: 22
gaacactcaa cacaccttat                                               20

<210> SEQ ID NO 23
<211> LENGTH: 20
<212> TYPE: DNA
<213> ORGANISM: Saccharomyces cerevisiae

<400> SEQUENCE: 23
gaacactcaa caaccttat                                                20

<210> SEQ ID NO 24
<211> LENGTH: 20
<212> TYPE: DNA
<213> ORGANISM: Saccharomyces cerevisiae

<400> SEQUENCE: 24
gaacactcaa caaaacttat                                               20

<210> SEQ ID NO 25
<211> LENGTH: 20
<212> TYPE: DNA
<213> ORGANISM: Saccharomyces cerevisiae

<400> SEQUENCE: 25
gaacactcaa caaacattat                                               20

<210> SEQ ID NO 26
<211> LENGTH: 20
<212> TYPE: DNA
<213> ORGANISM: Saccharomyces cerevisiae

<400> SEQUENCE: 26
gaacactcaa caaaccgtat                                               20

<210> SEQ ID NO 27
<211> LENGTH: 20
<212> TYPE: DNA
<213> ORGANISM: Saccharomyces cerevisiae

<400> SEQUENCE: 27
gaacactcaa caaacctgat                                               20

<210> SEQ ID NO 28
<211> LENGTH: 20
<212> TYPE: DNA
<213> ORGANISM: Saccharomyces cerevisiae

<400> SEQUENCE: 28
gaacactcaa caaaccttct                                               20

-continued

```
<210> SEQ ID NO 29
<211> LENGTH: 20
<212> TYPE: DNA
<213> ORGANISM: Saccharomyces cerevisiae

<400> SEQUENCE: 29
gaacactcaa caaaccttag                                                   20

<210> SEQ ID NO 30
<211> LENGTH: 19
<212> TYPE: DNA
<213> ORGANISM: Saccharomyces cerevisiae

<400> SEQUENCE: 30
aacggcttaa ggttctctt                                                    19

<210> SEQ ID NO 31
<211> LENGTH: 19
<212> TYPE: DNA
<213> ORGANISM: Saccharomyces cerevisiae

<400> SEQUENCE: 31
aagagaacct taagccgtt                                                    19

<210> SEQ ID NO 32
<211> LENGTH: 20
<212> TYPE: DNA
<213> ORGANISM: Saccharomyces cerevisiae

<400> SEQUENCE: 32
cgcatagtcg gcagctttct                                                   20

<210> SEQ ID NO 33
<211> LENGTH: 20
<212> TYPE: DNA
<213> ORGANISM: Saccharomyces cerevisiae

<400> SEQUENCE: 33
agaaagctgc cgactatgcg                                                   20

<210> SEQ ID NO 34
<211> LENGTH: 20
<212> TYPE: DNA
<213> ORGANISM: Saccharomyces cerevisiae

<400> SEQUENCE: 34
ttcggacgtt gaacactcaa                                                   20

<210> SEQ ID NO 35
<211> LENGTH: 20
<212> TYPE: DNA
<213> ORGANISM: Saccharomyces cerevisiae

<400> SEQUENCE: 35
ttgagtgttc aacgtccgaa                                                   20

<210> SEQ ID NO 36
<211> LENGTH: 20
<212> TYPE: DNA
<213> ORGANISM: Saccharomyces cerevisiae

<400> SEQUENCE: 36
caaaccttat ctagtgccca                                                   20
```

```
<210> SEQ ID NO 37
<211> LENGTH: 20
<212> TYPE: DNA
<213> ORGANISM: Saccharomyces cerevisiae

<400> SEQUENCE: 37
tgggcactag ataaggtttg                                          20

<210> SEQ ID NO 38
<211> LENGTH: 20
<212> TYPE: DNA
<213> ORGANISM: Saccharomyces cerevisiae

<400> SEQUENCE: 38
accaggtgtg cttctacgag                                          20

<210> SEQ ID NO 39
<211> LENGTH: 20
<212> TYPE: DNA
<213> ORGANISM: Saccharomyces cerevisiae

<400> SEQUENCE: 39
ctcgtagaag cacacctggt                                          20

<210> SEQ ID NO 40
<211> LENGTH: 20
<212> TYPE: DNA
<213> ORGANISM: Saccharomyces cerevisiae

<400> SEQUENCE: 40
tcttgctcac tcagacacac                                          20

<210> SEQ ID NO 41
<211> LENGTH: 20
<212> TYPE: DNA
<213> ORGANISM: Saccharomyces cerevisiae

<400> SEQUENCE: 41
gtgtgtctga gtgagcaaga                                          20

<210> SEQ ID NO 42
<211> LENGTH: 22
<212> TYPE: DNA
<213> ORGANISM: Saccharomyces cerevisiae

<400> SEQUENCE: 42
ctatccctat tgttacggct at                                       22

<210> SEQ ID NO 43
<211> LENGTH: 22
<212> TYPE: DNA
<213> ORGANISM: Saccharomyces cerevisiae

<400> SEQUENCE: 43
atagccgtaa caatagggat ag                                       22

<210> SEQ ID NO 44
<211> LENGTH: 19
<212> TYPE: DNA
<213> ORGANISM: Saccharomyces cerevisiae

<400> SEQUENCE: 44
aggtctcttc gcatagtcg                                           19
```

<210> SEQ ID NO 45
<211> LENGTH: 20
<212> TYPE: DNA
<213> ORGANISM: Saccharomyces cerevisiae

<400> SEQUENCE: 45
cgactatgcg aagagaacct                                           20

<210> SEQ ID NO 46
<211> LENGTH: 20
<212> TYPE: DNA
<213> ORGANISM: Saccharomyces cerevisiae

<400> SEQUENCE: 46
gcagctttct ttcggacgtt                                           20

<210> SEQ ID NO 47
<211> LENGTH: 20
<212> TYPE: DNA
<213> ORGANISM: Saccharomyces cerevisiae

<400> SEQUENCE: 47
aacgtccgaa agaaagctgc                                           20

<210> SEQ ID NO 48
<211> LENGTH: 20
<212> TYPE: DNA
<213> ORGANISM: Saccharomyces cerevisiae

<400> SEQUENCE: 48
ataaggtttg ttgagtgttc                                           20

<210> SEQ ID NO 49
<211> LENGTH: 20
<212> TYPE: DNA
<213> ORGANISM: Saccharomyces cerevisiae

<400> SEQUENCE: 49
ctagtgccca accaggtgtg                                           20

<210> SEQ ID NO 50
<211> LENGTH: 20
<212> TYPE: DNA
<213> ORGANISM: Saccharomyces cerevisiae

<400> SEQUENCE: 50
cacacctggt tgggcactag                                           20

<210> SEQ ID NO 51
<211> LENGTH: 20
<212> TYPE: DNA
<213> ORGANISM: Saccharomyces cerevisiae

<400> SEQUENCE: 51
cttctacgag tcttgctcac                                           20

<210> SEQ ID NO 52
<211> LENGTH: 20
<212> TYPE: DNA
<213> ORGANISM: Saccharomyces cerevisiae

<400> SEQUENCE: 52

-continued

```
gtgagcaaga ctcgtagaag                                               20

<210> SEQ ID NO 53
<211> LENGTH: 20
<212> TYPE: DNA
<213> ORGANISM: Saccharomyces cerevisiae

<400> SEQUENCE: 53
tcagacacac ctatccctat                                               20

<210> SEQ ID NO 54
<211> LENGTH: 20
<212> TYPE: DNA
<213> ORGANISM: Saccharomyces cerevisiae

<400> SEQUENCE: 54
atagggatag gtgtgtctga                                               20

<210> SEQ ID NO 55
<211> LENGTH: 12
<212> TYPE: DNA
<213> ORGANISM: Saccharomyces cerevisiae

<400> SEQUENCE: 55
tgttacggct at                                                       12

<210> SEQ ID NO 56
<211> LENGTH: 12
<212> TYPE: DNA
<213> ORGANISM: Saccharomyces cerevisiae

<400> SEQUENCE: 56
atagccgtaa ca                                                       12

<210> SEQ ID NO 57
<211> LENGTH: 17
<212> TYPE: DNA
<213> ORGANISM: Artificial Sequence
<220> FEATURE:
<221> NAME/KEY: misc_feature
<222> LOCATION: ()..()
<223> OTHER INFORMATION: synthetic construct for cloning

<400> SEQUENCE: 57
ccattcaggc tgcgcaa                                                  17

<210> SEQ ID NO 58
<211> LENGTH: 27
<212> TYPE: DNA
<213> ORGANISM: Artificial Sequence
<220> FEATURE:
<221> NAME/KEY: misc_feature
<222> LOCATION: ()..()
<223> OTHER INFORMATION: synthetic construct for cloning

<400> SEQUENCE: 58
gctttctttc gaagcttaac ggcttaa                                       27

<210> SEQ ID NO 59
<211> LENGTH: 19
<212> TYPE: DNA
<213> ORGANISM: Artificial Sequence
<220> FEATURE:
<221> NAME/KEY: misc_feature
<222> LOCATION: ()..()
<223> OTHER INFORMATION: synthetic construct for cloning
```

```
<400> SEQUENCE: 59
tccacctttg tgtgccatc                                                    19

<210> SEQ ID NO 60
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: synthetic construct for cloning

<400> SEQUENCE: 60
gaacatacga caaaccttat                                                   20

<210> SEQ ID NO 61
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: synthetic construct for cloning

<400> SEQUENCE: 61
ataaggtttg tcgtatgttc                                                   20
```

HYPOXIA RESPONSIVE TRANSCRIPTION ENHANCER ELEMENT FROM YEAST

CROSS REFERENCE TO RELATED APPLICATIONS

The present application claims the benefit of U.S. provisional application No. 60/260,678, filed on Jan. 11, 2001.

STATEMENT OF GOVERNMENT SUPPORT

The work leading to this invention was supported by the U.S. Government under NIH Grant No. DK45098 provided by the Department of Health and Human Services. The U.S. Government therefore has certain rights in the invention.

FIELD OF THE INVENTION

The present invention is directed to a nucleic acid element that enhances gene expression in yeast in response to hypoxic conditions. This element may be ligated to genes to enhance recombinant protein production both in yeast and in other eukaryotic cells.

BACKGROUND OF THE INVENTION

The ability to induce the expression of specific genes in response to hypoxia is a characteristic common to both prokaryotic and eukaryotic cells (Bunn, et al. *Physiol. Rev.* 76:839–885 (1996); Ebert, et al. *Blood* 94:1864–1877 (1999); Levy, et al. *J. Biol. Chem.* 270:13333–13340 (1995); Semenza, et al. *Mol. Cell. Biol.* 12:5447–5454 (1992)). Certain factors appear to mimic hypoxia and induce the expression of the same genes induced in response to low oxygen levels. These inducers include transition metals (e.g., cobalt and nickel) and iron chelators (Goldberg, et al. *Science* 42:1412–1415 (1988); Horiguchi, et al. *Biochim. Biophys. Acta* 1495:231–236 (2000); and Huang, et al. *J. Biol. Chem.* 271:32253–32259 (1996)). In addition, at least one factor, carbon monoxide, has been found to inhibit the expression of hypoxia-induced genes (Huang, et al. *J. Biol. Chem.* 274:9038–9044 (1999)).

Yeast such as *Saccharomyces cerevisiae*, respire in the presence of oxygen but ferment under anaerobic conditions. Not surprisingly, these organisms have evolved sophisticated molecular mechanisms involving oxygen dependent gene regulation. Several yeast genes, exemplified by ANB1, have been shown to be upregulated by complete anaerobiosis (Zitomer, et al. *Microbiol Rev.* 5:1–11 (1992)). In addition, other genes exhibit increased expression at low oxygen tensions, before complete anaerobic conditions are reached (Kwast, et al. *Proc. Nat.'l Acad. Sci. USA* 96:5446–5451 (1999)). The identification of the mechanisms by which yeast and other organisms regulate gene expression in response to low levels of oxygen should provide new insights into biological adaptations used for survival and new opportunities for controlling the cellular production of recombinant genes.

SUMMARY OF THE INVENTION

The present invention is based upon the discovery of a distinct hypoxia responsive enhancer element (HREE, also referred to herein as a low oxygen response element, or "LORE") that helps regulate the rate at which mRNA is transcribed from the OLE1 gene in yeast in response to low levels of oxygen. This element may be combined with other genes to increase recombinant protein production both in yeast and in other eukaryotic cells. The element responds both to low levels of oxygen (hypoxic conditions) and to essentially a complete absence of oxygen (anaerobic conditions). For the purposes of the present invention, reference to "hypoxia" or "hypoxic conditions" will include "anaerobic conditions" unless the context of usage indicates otherwise.

In its first aspect, the invention is directed to a substantially pure HREE DNA molecule consisting essentially of either the sequence ACYCAACAA (SEQ ID NO: 1) or GAACACYCAACAAACCTTAT (SEQ ID NO: 2). The symbol "Y" indicates that the designated nucleotide may be either T or C. As used herein, the term "consisting essentially of" means that, starting with either SEQ ID NO: 1 or SEQ ID NO: 2, the invention includes minor changes in the sequences provided that such changes do not alter the basic biological characteristics of the elements with respect to their ability to induce gene expression in response to hypoxia and provided that the mutated product maintains at least a 50% structural homology to either SEQ ID NO: 1 or SEQ ID NO: 2. For example, mutated elements that evidenced a substantial (e.g. 70%) loss in their ability to induce expression would not be part of the invention. In this regard, it should be noted that SEQ ID NO: 1 forms a 9 nucleotide core within SEQ ID NO: 2 being flanked at its 5' end by the sequence GAAC, and its 3' end by the sequence CCTTAT. Core sequences joined to either all or part of these flanking sequences are encompassed by the invention. For example, SEQ ID NO: 1 may be flanked at its 5' end by C, AC, AAC, or GAAC. Similarly, it may be flanked at its 3' end by C, CC, CCT, CCTT, CCTA, or CTTAT.

The DNA sequence elements described above may be included in a vector for recombinantly expressing a peptide or protein in eukaryotic cell. The vector includes a promoter active in the eukaryotic cell, a hypoxia responsive enhancer element as described above, and a DNA sequence encoding the peptide or protein. The latter should be operably linked to the promoter. In addition, the sequence encoding the peptide or protein should be non-homologous to HREE. The term "non-homologous" indicates that the HREE element is joined to a gene other than one it would normally be operably linked to in nature, e.g. the element must be joined to something other than the yeast OLE1 gene. The vector may be used to transform an appropriate host cell for the purpose of producing recombinant protein. Preferably, the host cell is a yeast and the promoter used in the vector is active in yeast cells. The most preferred promoter is the CYC1 basal promoter.

In another aspect, the invention is directed to a method for recombinantly producing a peptide or protein in which host cells transformed with the vector discussed above are grown under anaerobic conditions. In certain instances, such cells may have direct utility. For example, yeast cells might be transformed with a vector for the expression of a gene that enhances alcohol production during fermentation. In other instances, the method may include the purification of recombinant protein or peptide either directly from host cells or, preferably, from the medium surrounding the host cells. These methods for producing peptides or proteins may include exposing the transformed host cells to an agent that helps to induce recombinant gene expression. In particular, cells may be exposed to either transition metals or to iron chelators. The most preferred transition metals are cobalt and nickel.

The present invention also encompasses certain variations on the method for recombinantly producing peptides or proteins discussed above. In one embodiment, host cells transformed with an HREE-containing vector are first grown under aerobic conditions and recombinant expression of peptide or protein is then induced by exposing the cells to anaerobic conditions. Again, the preferred host cells are yeast and these may either be used directly or the recombinant protein can be purified prior to use.

In another variation, host cells are first grown under aerobic conditions and gene expression is then induced by exposing them either to a transition metal such as cobalt or nickel or by exposing them to an iron chelator. It is also possible to combine these methods so that the expression of genes is controlled both by changing oxygen availability and by altering the concentration of inducing agents.

BRIEF DESCRIPTION OF THE DRAWINGS

FIG. 1: Summary of the DNA binding ability of mutant LOREs. The first row of the figure shows the wild type (WT) LORE sequence. G347T to T328G are examples of single nucleotide mutations in the LORE at various positions. Values for DNA binding represent binding activities of the LORE binding factor(s) to the various mutant sites. Values represent percentages relative to the wild type LORE in an EMSA, quantitated with a Phosphorimager; * indicates altered EMSA pattern. The nucleotides shadowed (vertically) indicate the positions important for hypoxia induced complex formation in vitro. The figure shows the following sequences:

```
GAACACTCAACAAACCTTAT    (SEQ ID NO:3)
TAACACTCAACAAACCTTAT    (SEQ ID NO:4)
GCACACTCAACAAACCTTAT    (SEQ ID NO:5)
GACCACTCAACAAACCTTAT    (SEQ ID NO:6)
GAAAACTCAACAAACCTTAT    (SEQ ID NO:7)
GAACCCTCAACAAACCTTAT    (SEQ ID NO:8)
GAACTCTCAACAAACCTTAT    (SEQ ID NO:9)
GAACAATCAACAAACCTTAT    (SEQ ID NO:10)
GAACACGCAACAAACCTTAT    (SEQ ID NO:11)
GAACACCCAACAAACCTTAT    (SEQ ID NO:12)
GAACACACAACAAACCTTAT    (SEQ ID NO:13)
GAACACTAAACAAACCTTAT    (SEQ ID NO:14)
GAACACTCCACAAACCTTAT    (SEQ ID NO:15)
GAACACTCACCAAACCTTAT    (SEQ ID NO:16)
GAACACTCAAAAACCTTAT     (SEQ ID NO:17)
GAACACTCAATAAACCTTAT    (SEQ ID NO:18)
GAACACTCAACCAACCTTAT    (SEQ ID NO:19)
GAACACTCAACTAACCTTAT    (SEQ ID NO:20)
GAACACTCAACGAACCTTAT    (SEQ ID NO:21)
GAACACTCAACACACCTTAT    (SEQ ID NO:22)
GAACACTCAACAACCCTTAT    (SEQ ID NO:23)
GAACACTCAACAAAACTTAT    (SEQ ID NO:24)
GAACACTCAACAAACATTAT    (SEQ ID NO:25)
GAACACTCAACAAACCGTAT    (SEQ ID NO:26)
```

-continued
```
GAACACTCAACAAACCTGAT    (SEQ ID NO:27)
GAACACTCAACAAACCTTCT    (SEQ ID NO:28)
GAACACTCAACAAACCTTAG.   (SEQ ID NO:29)
```

DEFINITIONS

The invention description provided herein uses a number of terms that refer to recombinant DNA technology. In order to provide a clear and consistent understanding of the specification and claims, including the scope to be given such terms, the following definitions are provided.

Substantially pure: As used herein, the term "substantially pure" refers to a biological component, protein or nucleic acid, that has been separated from other accompanying biological components so that, typically, it comprises at least 85% of a sample, with greater percentages being preferred. Many means are available for assessing the purity of nucleic acids and proteins within a sample, including analysis by polyacrylamide gel electrophoresis chromatography and analytical centrifugation.

Operably linked: The term "operably linked" refers to genetic elements that are joined in a manner that enables them to carry out their normal functions. For example, a gene is operably linked to a promoter when its transcription is under the control of the promoter and the transcript produced is correctly translated into the protein normally encoded by the gene. The HREE element is operably linked to a gene when it is capable of inducing or enhancing expression of the gene in response to hypoxia.

Promoter: A promoter is the DNA sequence at which transcription is initiated. If the promoter is of the inducible type, then its activity increases in response to an inducing agent.

Expression: Expression is the process by which a polypeptide is produced from DNA. The process involves the transcription of the gene into mRNA and the subsequent translation of the mRNA into a polypeptide.

Host: Any prokaryotic or eukaryotic cell that is the recipient of an expression or cloning vector is the "host" for that vector. Examples of cells that can serve as hosts are well known in the art, as are techniques for cellular transformation (See e.g., Sambrook, et al. *Molecular Cloning: A Laboratory Manual,* 2nd ed. Cold Spring Harbor (1989)).

Cloning Vector: A cloning vector is a DNA sequence (typically a plasmid or phage) which is able to replicate autonomously in a host cell, and which is characterized by one or a small number of restriction endonuclease recognition sites. A foreign DNA fragment may be spliced into the vector at these sites in order to bring about the replication and cloning of the fragments. The vector may contain one or more markers suitable for use in the identification of transformed cells. For example, markers may provide tetracycline or ampicillin resistance.

Expression vector: An expression vector is similar to a cloning vector but is capable of inducing the expression of DNA that has been cloned into it after transformation into a host. The cloned DNA is usually placed under the control of (i.e., operably linked to) certain regulatory sequences such as promoters or enhancers.

DETAILED DESCRIPTION OF THE INVENTION

The present invention is directed to an hypoxia-responsive enhancer element (HREE) that was first identified in connection with the OLE1 gene of S. cerevisiae. The element is defined by its structure as shown in SEQ ID NO: 1 and SEQ ID NO: 2. However, it will be understood that the invention encompasses not only sequences identical to those shown but also sequences that are essentially the same as evidenced, by their retaining the basic functional characteristic of enhancing the expression of an operably linked gene in cells exposed to hypoxic conditions.

The core of the HREE element (SEQ ID NO: 1) is 9 nucleotides in length and can easily be made using standard synthetic methods. This core may be extended at its 5' end by all or part of the sequence GAAC. It may be extended at its 3' end by all or part of the sequence CCTTAT. If both of these flanking elements are fully included, then a 20 nucleotide sequence is produced which corresponds to SEQ ID NO: 2.

Once the HREE element has been synthesized, it may be incorporated into an expression vector using methods that are standard in the art. The exact position of the HREE element within the vector is not critical to the invention and it may lie either 3' or 5' to the promoter sequence and to the gene undergoing transcription. Examples of eukaryotic promoters that may be used include the promoter of the mouse metallothionein I gene (Hamer, et al. *J. Mol. Appl. Gen.* 1:273 (1982)); the immediate early and TK promoters of Herpes virus (Yao, et al. *J. Virol.* 69:6249–6258 (1995)); the SV 40 early promoter (Benoist, et al. *Nature* 290:304–310 (1981)); and the human CMV promoter (Boshart, et al. *Cell* 41:521–530 (1985)). Full length or minimal promoters may be used and other regulatory elements may be included.

Once a vector DNA sequence has been prepared, it may be introduced into cells by any means known in the art, including: calcium phosphate precipitation, microinjection, electroporation, liposomal transfer, or viral transfer. Large numbers of recipient cells may then be grown in a medium which selects for vector-containing cells. These cells may be used directly or the expressed recombinant protein may be purified in accordance with conventional methods such as extraction, precipitation, chromatography, affinity methods, electrophoresis and the like. The exact procedure used will depend upon the specific protein produced and the specific expression system utilized.

Most preferably, yeast cells will be used for recombinantly producing protein. Methods for constructing expression vectors functional in yeast and for using yeast cells to produce proteins are well known in the art and specific model procedures are provided below in the Examples section. Also provided are examples of methods for growing yeast, and for inducing expression by hypoxia or by the addition of inducing agents. Optimal conditions can be readily determined for individual systems using standard scientific procedures. However, as a guideline, yeast cells should generally be induced to express the HREE-associated elements or genes by maintaining them in 1 % $O_2$ or less for several, e.g., 6–12, hours. When inducing agents such as cobalt or nickel are used, they should be added at a concentration that is not toxic to cells. In general, a concentration of cobalt in the range of 300 $\mu$M to 1 mM should be effective. Similarly, nickel in the range of 200 $\mu$M to 600 $\mu$M should usually produce an effective induction of protein synthesis. When an iron chelator is used for induction, a titration may be carried out to find an optimal concentration for inducing gene expression. As discussed in the Examples section, the chelator 1,10-Ph was found to substantially increase gene expression after 6 hours of incubation when used in the concentration range of 2–8 $\mu$g/ml.

It is expected that the present invention will be of particular use to scientists and companies engaged in the large scale production of recombinant proteins using eukaryotic cells, particularly yeast. In addition, brewery companies may benefit from the invention by engineering yeast to express large amounts of selected genes under the anaerobic conditions present during fermentation. Systems could be designed in which constructs for expressing recombinant protein are either integrated into a yeast chromosome or left free as a plasmid.

Another use for the HREE element will be in the treatment of cancer patients. It is well known in the art that tumors derive their energy anaerobically compared to normal cells. The relatively low oxygen concentrations within cancer cells can be used in conjunction with the HREE element as a means for targeting therapeutic agents. For example, the HREE may be part of a vector for the expression of a gene that is toxic to cells when expressed. If this vector is delivered systemically to a patient, it may be taken up by many cells, but expression will be much higher in those with low concentrations of oxygen, i.e., in cells that are cancerous. This same approach may be taken for diagnostic purposes, e.g., locating sites of metastasis. In this case, the HREE element would be part of a vector in which a gene is expressed that can be easily detected. For example, it might be joined to a fusion protein made up of a cell surface protein and avidin. Cells expressing this fusion protein might then be detected using biotin that has been labeled with a compound that can be detected using in vivo imaging techniques.

EXAMPLES

I. Materials and Methods

Media, Chemicals, and Enzymes

Yeast strains were grown in YPD medium (Bio101, Inc. MA) or SC dropout medium, depending on the plasmid selectable markers. LB was used for bacteria growth purposes. Ampicillin was used as necessary at 50 $\mu$g/ml unless indicated otherwise. o-nitrophenyl-β-galactopyranoside (ONPG) was obtained from ICN Biochemicals Inc. (OH) or Sigma Chemical Co (MO). Radiolabeled compounds were purchased from DuPont NEN (NJ). Formamide, dextran sulfate and Denhardt's solution were bought from American Bioanalytical (MA). Acrylamide, bisacrylamide, TEMED and protein molecular mass markers were from BioRad (CA). Ammonium sulfate, phenylmethylsulfonyl fluoride (PMSF), $CoCl_2$, $NiCl_2$, 1,10-phenanthroline and NP-40 were obtained from Sigma Chemical Co (MO). SeaKem ME agarose was from FMC Bioproducts (ME). T4 polynucleotide kinase (PNK) and dNTPs were purchased from Promega Corporation (WI). Shrimp alkaline phosphatase (SAP) and Taq polymerase were purchased from Roche Molecular Biochemicals (IN); other restriction enzymes were from New England BioLabs (MA). All enzymes were used according to the manufacturer's instructions.

Oligonucleotide Synthesis

Oligonucleotides were synthesized by Integrated DNA Inc. Necessary restriction sites for cloning were added at the 5' ends of primers and were preceded by 3 to 6 nucleotides for efficient digestion. Paired oligonucleotides used for direct cloning possess a phosphate group at the 5' end. Table 1 shows the nucleotide sequences used for polymerase chain reaction (PCR), Northern blot assay, EMSA, cloning and site-directed mutagenesis.

Plasmids and Plasmid Construction

Plasmids used in this study are shown in Table 2. The construction of several of the OLE1 promoter-lacZ fusion deletion series has been described previously (Choi, et al., *J. Biol. Chem.* 271:3581–3589 (1996)). Construction of pAM6, pAM7, pAM10 and pAM16 vectors containing the OLE1 low oxygen response element (LORE) sequences −347 to −328 relative to the ATG translational start codon with the A of the codon designated as +1) was performed by inserting the synthetic paired oligonucleotides (10–5' and 10–3') into the XhoI restriction site of pTBA30, the CYC1 basal promoter-lacZ fusion vector. pAM16 contains one LORE copy in the −347 to −328 forward or (+) orientation 5' to the basal CYC1 promoter-lacZ fusion. pAM7 has one LORE copy in the −328 to −347 reverse or (+) orientation. pAM6 contains a tandem repeat of the LORE in the (+) orientation. pAM10 was generated by inserting the synthetic paired oligonucleotides (yd-19 and yd-20) into the XhoI restriction site of pTBA30. The LORE in this plasmid has three mutations. Plasmid pAM4 is the p62::934 derivative with three nucleotide substitutions in the LORE region (-C342T, -T341A and -A339G) prepared utilizing three step PCR with oligonucleotides containing site-directed mutations. Two PCR reactions with appropriate pairs of mutant primers (PCR1 : yd–8 and yd-20 and PCR2: yd–19 and lacZ-3') and Taq DNA polymerase were carried out as recommended by Roche Molecular Biochemicals (IN) in 100 $\mu$l reactions, using 1 ng of p62::934 as a template in a PTC-100 thermal cycler for 30 cycles (1 min at 94° C., 1 min at 55° C., 1 min at 72° C.), followed by 7 min at 72° C. The PCR products were purified from a 1.0% agarose gel using a Qiaex DNA extraction kit (Qiagen, Calif.). Then, PCR products 1 and 2 were annealed and amplified as above with primer yd-8 and lacZ-3'. The resulting PCR products were purified as above and digested with restriction enzymes HindIII and SalI. Finally this PCR product was cloned into HindIII and SalI pretreated p62::934 plasmid to generate pAM4. All the constructs were verified by DNA sequencing. The promoter deletion constructs were transformed into wild-type strain RZ53–6 for subsequent β-galactosidase assays.

Strains and Growth Conditions

Table 2 shows the yeast strains used in these studies. Yeast cells containing lacZ fusion plasmids were grown at 30° C. on uracil dropout medium containing dextrose (Treco, et al., In *Current Protocols in Molecular Biology*, Ausubel, et al., eds., pp. 13.2.1–13.2.12, John Wiley & Sons, New York (1997)). For unsaturated fatty acid repression analysis, yeast were grown in medium supplemented with 1% tergitol as described previously (Choi, et al., *J. Biol. Chem.* 271:3581–3589 (1996)). Cells were grown in the presence of UFAs for 6 hours prior to the β-galactosidase assays. Plasmid amplifications and bacterial transformations were performed using *Escherichia coli* strain DH5 (Invitrogene Corp.). Yeast transformations were performed by the method of Elble (*BioTechniques* 13:18–20 (1992)). Preparative cultures were grown aerobically in a shaker at 200 rpm (Innova 4000 incubator shaker, New Brunswick Scientific. NJ) at 30° C. to mid-logarithmic phase. For experiments assessing yeast under hypoxic conditions, mid-logarithmic phase preparative cultures were used to inoculate special air-tight flasks with inlet and outlet ports to allow for equilibration with the appropriate gas mixtures. Cultures were exposed to a continuous flow of hydrated medical grade nitrogen (BOC Gases, MA), unless otherwise specified, for 6 hours after inoculating the medium via the inlet port. Of note, medical grade nitrogen is contaminated with trace amounts of $O_2$ (less than 1%). The percentage of saturated $O_2$ in each flask was confirmed by using an oxygen monitor (G. C. Industries, Inc.) attached to the outlet port of each culture. For experiments assessing yeast exposed to cobalt, cobalt chloride was added to the cultures at a concentration of 400 $\mu$M unless otherwise noted. Cells were exposed to cobalt for a period of 6 hours prior to harvesting. The flasks contained a volume of medium that was approximately ⅕ the flask volume. All experiments were performed with yeast in logarithmic growth phase in a shaker (200 rpm) at 30° C. Growth was monitored by measuring the yeast $OD_{600}$ at the completion of each experiment.

β-Galactosidase Assays

Assays of cells containing plasmids derived from the OLE1 promoter-lacZ fusion p62 constructs were performed as described previously (Reynolds, et al., In *Current Protocols in Molecular Biology*, Ausubel, et al. eds., pp. 13.6.2–13.6.3, John Wiley & Sons, New York (1997)). Cell densities for these assays were determined by measurement at $OD_{600}$. Transformants were assayed for each of the plasmid constructs listed in Table 2. β-galactosidase activities reported here are the results of at least two independent experiments. Each experimental assay was performed in quadruplicate.

DNA Sequencing

Plasmid templates for sequencing were isolated using a QIAprep spin purification kit (Qiagen). The fmol DNA sequencing system (Promega Corp.) was used for sequencing according to its technical manual. Reactions were run on 6% sequencing gels, which were dried and exposed to X-OMAT AR film (Kodak, NY) to visualize the sequence.

Yeast Extract Preparation

Haploid yeast (*S. cerevisiae*, strain RZ53–6 ) were cultured in 1-liter flasks containing 200 ml of YPD (1% yeast extract, 2% peptone, 2% dextrose) either under normoxic or hypoxic conditions, harvested at midlog phase ($OD_{600}$=0.8), and lysed by vortexing with glass beads according to published protocols (Pfeifer, et al., *Cell* 49:9–18 (1987)). Following addition of ammonium sulfate to 40% and incubation on a rocker table at 4° C. for 30 minutes, the precipitate was collected by centrifugation at 14,000 rpm in a microfuge at 4° C. for 10 minutes. The pellet was resuspended in storage buffer (20 mM HEPES, pH8.0; 5 mM EDTA; 20% (v/v) glycerol; 1 mM PMSF; 7 mM β-mercaptoethanol) and stored frozen at −80° C. The soluble protein concentration was determined using a Bradford dye binding assay (BioRad, CA).

Electrophoretic Mobility Shift Assay (EMSA)

EMSAs were performed essentially as described by Carey (Carey, *Methods Enzymol.* 208:103–117 (1991)) utilizing synthetic paired oligonucleotides (e.g., 10–5' and 10–3') as a probe or a probe containing the LORE sequence made by PCR using p62::934 as the template with $^{32}$P-labeled oligonucleotides 1–5' and yd-10 (−397 to −234) as the primers. Synthetic paired oligonucleotides were end labeled using polynucleotide kinase and purified using a Sephadex G-25 spin column (Roche Molecular Biochemicals, IN) to remove unincorporated nucleotide. Probes made by PCR were purified away from labeled primers, [$\gamma$-$^{32}$P]ATP and Taq polymerase using a QIAquick spin PCR purification kit (Qiagen). The concentration of each probe was determined on an ethidium bromide stained agarose-mini gel (Maniatis, et al., *Molecular Cloning: A Laboratory Manual*, Cold Spring Harbor Laboratory Press, Cold Spring Harbor, N.Y. (1982)). In each reaction, 10–20 ng of probe was used. Binding reactions were in 40 $\mu$l of buffer H (25 mM HEPES, pH 7.5 at room temperature; 0.5 mM EDTA, 0.5 mM DTT, 0.5 mM $MgCl_2$, 1 mM $CaCl_2$, 50 mM NaCl, 7% glycerol, 1% NP40, 15 ng/$\mu$L poly-dAdT) for 20 min at room temperature. Proteins were diluted into binding buffer on ice immediately before use. Reactions were loaded on 5% acrylamide gels (29:1), 0.5× TBE, and run for 3 hours at 4°

C. at 15 V/cm. Gels were dried and exposed to X-OMAT AR film (Kodak) to visualize the shifted bands.

RNA Isolation and Northern Blot Analysis

Total yeast RNA was isolated as described previously (Collart, et al., In *Current Protocols in Molecular Biology*, Ausubel, et al., pp. 13.12.1–13.12.5, John Wiley & Sons, New York (1997)). Equal amounts (15 µg) of total RNA were analyzed by Northern blots according to standard procedures for separation of RNA using 1% formaldehyde gels (Collart, et al., In *Current Protocols in Molecular Biology*, Ausubel, et al., eds, pp. 13.12.1–13.12.5, John Wiley & Sons, New York (1997)). RNA from the gels was transferred to Nytran Plus membranes (Schleicher & Schuell Inc, NH) in 10× SSC overnight. Prehybridization, hybridization, and washing of membranes were performed as described (Brown, et al., In *Current Protocols in Molecular Biology*, Ausubel, et al., eds., pp. 4.9.1–4.9.14, John Wiley & Sons, New York (1997)). Northern blots were quantified using a phosphorimager (Molecular Dynamics) and autoradiographs were also prepared on X-OMAT AR film (Kodak, NY).

To make radiolabeled cDNA probes for other genes of interest (including ACT1 as a control), yeast genomic DNA prepared by the rapid isolation of yeast chromosomal DNA protocol (Hoffman, In *Current Protocols in Molecular Biology*, Ausubel, et al. eds pp. 13.11.2–13.11.4, John Wiley & Sons, New York (1997)) was subjected to PCR with appropriate pairs of primers for the particular genes of interest. The PCR products were first purified using a QIAquick spin PCR purification kit (Qiagen), separated by agarose gel electrophoresis in 1× TAE, then purified by Qiagen gel extraction kit (Qiagen) according to manufacturer's recommendations.

For the detection of OLE1 mRNA, a radiolabeled DNA probe was made using a 0.5 kb EcoRI fragment from the OLE1 protein coding sequence. For an internal control of cellular mRNA levels, a 1-kb HindIII-KpnI fragment of the *S. cerevisiae* phosphoglycerate kinase gene (PGK1) was isolated from plasmid pRIPIPGK. All DNA fragments were separated by agarose gel electrophoresis in 1× TAE and purified by Qiagen gel extraction kit (Qiagen) according to the manufacturer's recommendations. The purified DNA fragments were labeled to high specific activity with [$^{32}$P] dCTP by the random primer extension method using Ready to Go DNA labeling beads (Amersham Pharmaceutical Biotech) reaction kit. Unincorporated nucleotides were removed from the sample using a Sephadex G-50 spin column (Roche Molecular Biochemicals). Specific activity of labeled probes was determined by liquid scintillation counting.

II. Results

A. Hypoxia, the transition metals cobalt and nickel, and the iron chelator 1,10 phenanthroline increase OLE1 expression by Northern analysis and β-galactosidase reporter assay Previous studies have shown that OLE1 mRNA transcript levels are increased at low oxygen ($O_2$) tensions, below 0.5 µmol. Maximal expression, approaching a four fold increase over baseline normoxia, was observed following eight to ten hours of anoxia (Kwast, et al., *J. Exp. Biol.* 201 (Pt 8):1177–1195 (1998); Kwast, et al., *Proc. Nat'l Acad. Sci. USA* 96:5446–5451 (1999)). The present study confirmed that OLE1 mRNA is maximally expressed in the presence of trace $O_2$ (<1%) concentrations. Subsequently, this finding was extended utilizing a plasmid (p62::934) in which 934 bp of the OLE1 promoter is fused in frame with the lacZ gene. Less than a 2-fold induction over baseline levels in normoxia was observed in 1% $O_2$, although a 6-fold induction occurred at an extremely low $O_2$ tension.

In a similar fashion, the present study verified previous reports demonstrating increased levels of OLE1 mRNA following incubation of *S. cerevisiae* with increasing concentrations of cobalt chloride ($CoCl_2$) and nickel chloride ($NiCl_2$) in normoxia (Kwast, et al., *Proc. Nat'l Acad. Sci. USA* 96:5446–5451 (1999)). The concentrations used were similar to those used in the study of hypoxia-regulated mammalian genes such as Epo (Goldberg, et al., *Science* 242:1412–1415 (1988)). These data were confirmed with experiments utilizing the OLE1 promoter-lacZ reporter assay. The degree of induction approached that which has been previously reported, even though the metal concentrations were almost 10 fold lower. At 800 µM $CoCl_2$ and 450 µM $NiCl_2$, significant differences in the growth rate of the yeast compared to control cultures were observed in the present experiments, presumably due to direct toxicity of the culture by the metal on *S. cerevisiae*. It is not immediately apparent why the significantly lower metal concentrations used in the present studies appear to exert the same effect on OLE1 expression as the much higher concentrations employed in previous reports; differences in exposure time may be relevant.

Several mammalian hypoxia and transition metal-inducible genes are also upregulated by the iron chelator, desferrioxamine (reviewed in Bunn, et al., *Physiol. Rev.* 76:839–885 (1996)). The effect of iron chelation on OLE1 expression was therefore examined in the present studies. 1,10 Ph is an iron chelator that is routinely employed in studies with *S. cerevisiae*. Its affinity constant, K, for iron is $10^{21}$. It was found that exposure to 1,10 Ph for six hours resulted in a dose dependent increase in expression of OLE1, as assessed by Northern blot and OLE1 promoter-lacZ reporter data. Cell growth was unaffected by any of the concentrations tested.

OLE1 promoter deletion -lacZ constructs define a 142 bp region (−255 to 396 relative to the transcription start site) critical for induction by hypoxia and $CoCl_2$. A series of OLE1 promoter-lacZ fusion reporter constructs were transformed into the RZ53-6 strain and incubated in hypoxia, $CoCl_2$ or 1,10 Ph. It was found that the removal of bases −567 through −488 resulted in an 80-fold drop in enzyme activity under normoxia, suggesting the presence of an activating sequence in this region. Previous work has identified the fatty acid-regulated (FAR) element in this region (Choi, et al, *J. Biol. Chem.* 271:3581–3589 (1996)). In contrast, the deletion of sequences from −934 to −567 produced a small reduction in reporter gene expression under normoxia, hypoxia and cobalt treated conditions (within 2.7 fold). Deletions 3' to base −488 resulted in low basal reporter gene activities under normoxic conditions. However, removal of bases −488 through −396 did not dramatically affect the hypoxia- and cobalt-induced reporter gene expression. In contrast, the 142 bp region between −396 and −255 proved to be critical. Its removal essentially abolished the hypoxia induction and caused a significant reduction of $CoCl_2$-induced reporter gene expression. The observation that the deletion of sequence between −567 and −488 also resulted in about two-fold reduction of $CoCl_2$-induced reporter gene expression implies that additional regulatory elements necessary for complete $CoCl_2$-induced OLE1 gene expression may reside in this region.

B. Hypoxia-induced Activation Complex Formation with LORE

The analysis of the OLE1 promoter-lacZ fusion deletion series strongly suggests that the −255 to −396 region of the OLE1 promoter contains a cis element responsible for hypoxic induction. The possibility of an activation complex formed in hypoxic conditions was tested by EMSA using crude cell extracts from normoxia, hypoxia- and cobalt-treated yeast. A wild type OLE1 promoter DNA fragment containing base pairs −234 to −396 was generated using PCR as a probe for the assay. Two shifted bands ("B1" and "B3") were present in hypoxia and cobalt samples, though the $CoCl_2$ treated extracts were of somewhat lower intensity. B and B2 were constitutive and could be displaced by non-specific DNA. In order to further define the DNA region responsible for the hypoxia-inducible complex formation, a series of double stranded nucleotides 20 base pairs in length covering the entire −255 to −396 region of OLE1 DNA were synthesized and used as cold competitors for the hypoxia-inducible shifted bands (B1 and B3) in EMSA. A double-stranded oligonucleotide 10-5'/10-3' (Table 1-#10) could effectively compete out the shifted bands, whereas the remainder of the double-stranded oligonucleotides could not. Thus, oligonucleotide #10 appears to contain a site(s) for hypoxia- and $CoCl_2$-induced protein(s) binding and was designated as the low oxygen response element (LORE).

To further investigate the role of oligonucleotide #10 in hypoxia- and $CoCl_2$-induced complex formation, EMSAs were performed using end-labeled oligonucleotide #10 as a probe. It was found that crude extracts from both hypoxia and cobalt treated yeast form a specific complex with oligonucleotide #10 in vitro. When this shorter radiolabeled probe was used, band B2 was prominent whereas B3 was no longer present. This is consistent with the hypothesis that B3 complex formation requires additional element(s) outside of oligonucleotide #10. Further, when mutations were introduced in oligonucleotide #10, the intensity of the non-specific B2 was further enhanced. Shortened exposure time, however, confirmed that the specific hypoxia-induced B1 complex formation was not observed. No specific hypoxia- or $CoCl_2$-induced complex formation was observed using probe #8, confirming the previous EMSA competition assay.

C. LORE is Required for Hypoxia-induced OLE1 Expression In Vivo

A lacZ fusion reporter, pAM4, was constructed such that the full length OLE1 promoter possessed three mutations in the LORE region (−328 to −347). The requirement of an intact LORE for hypoxia-induced OLE1 expression was tested using the β-galactosidase assay in yeast containing the pAM4 reporter. In this reporter assay, an 8-fold decrease in the basal level of expression in normoxia compared with the non-mutated LORE reporter was observed. The mutated LORE sequence eliminated the 6-fold hypoxic-induction seen with the wild type reporter. This result is consistent with EMSA data which reveal no hypoxia-induced band shift when the same mutated fragment was utilized as a probe. However, the $CoCl_2$ dependent induction by reporter assay was not affected.

D. LORE is Sufficient for Hypoxia-Induced Gene Expression Under the Control of a Heterologous Promoter The LORE was fused to the basal CYC1 promoter-lacZ fusion plasmid pTBA30. Plasmid pAM6, carrying two copies of the LORE in tandem, was found to possess robust transcriptional activation under both hypoxic and cobalt-treated conditions with about 44-and 10-fold increases, respectively. A plasmid carrying one copy of the LORE in both orientations also substantially stimulated the reporter gene expression under both hypoxic and cobalt-treated conditions. In contrast, the plasmid pAM10, containing the CYC1 heterologous promoter with three mutations in LORE, did not show induction by either hypoxia or cobalt. Considerable variability in the basal expression of these constructs may have been due to differences in sequences related to orientation and copy number of insert.

E. LORE is Involved in OLE1 Repression Under Hypoxic Conditions by Unsaturated Fatty Acids (UFA)

Previous experiments demonstrated that FAR elements (−466 to −576) within the OLE1 promoter contribute to OLE1 repression by UFA in normoxic conditions (Choi, et al., *J. Biol. Chem.* 271:3581–3589 (1996)). However, when an OLE1-lacZ fusion containing a deleted FAR element was tested under hypoxia, the transactivation repression by UFA was still observed. That observation led us to examine whether the LORE plays a role in UFA induced OLE1 gene repression. It was found that the UFA linoleic acid (L.A.) can strongly repress normoxia-, hypoxia-, and cobalt-induced expression of the lacZ reporter plasmid pAM6 which contains two copies of the LORE in tandem. Inhibition showed a dose-response with an $IC_{50}$ ~20 μM. Similar dose-response inhibition was obtained using the unsaturated fatty acids gamma linolenic acid, oleic acid and arachidonic acid but not with the saturated fatty acid steric acid. Consistent with the (β-galactosidase assay, the OLE1 mRNA level was also dramatically repressed by L.A. when examined by Northern blot analysis. This repression in normoxia is consistent with previous studies. Again, UFA repression could not be overcome by incubation in hypoxic or cobalt-containing conditions. Crude extracts from L.A.-treated yeast were utilized for EMSA. It was found that the hypoxia-induced LORE complex formation was significantly suppressed with the disappearance of binding complex B1. The intensity of the basal expression of the B1 complex under normoxic condition was also repressed, implying that LORE may be involved in the basal expression of OLE1 as well. The non-specific band B2 was not affected.

F. Role of ROX1 in OLE1 Expression Under Hypoxic Conditions

ROX1 plays a significant role in the regulation of many anoxia-inducible yeast genes. Several studies have provided evidence that ROX1p functions as a repressor of anoxia-inducible gene expression under normoxic conditions. In addition, previous studies had postulated that ROX1 may contribute to OLE1 induction under anoxic conditions based on predicted potential ROX1p binding sites in the OLE1 promoter region. A ROX1 deletion mutant strain of RZ53–6 (RZ53–6 Δrox1) was, therefore, utilized to investigate the ROX1 effects on OLE1 expression under hypoxic conditions. The results of in vivo (β-galactosidase assays of reporter p62::934 in strains RZ53–6 and RZ53–6 Δrox1 showed that the basal expression of the reporter gene under normoxic conditions is essentially the same in the ROX1 deletion strain as in its parental strain. This suggests that ROX1 does not play a role as a repressor in the low basal level expression of OLE1 under normoxic conditions. Moreover, significant induction was still observed under hypoxic conditions (4.2 fold increase) and cobalt-treated conditions (5.1 fold increase) in the ROX1 deletion strain. On Northern blot analysis, the OLE1 mRNA level was induced in both strains under hypoxia- and cobalttreated conditions. Consistent with the in vivo transactivation data, it was also shown that the relative mRNA level of hypoxia and cobalt treated ROX1 deleted yeast was similar to that of wild-type. The basal OLE1 mRNA expression under normoxia was similar in both strains as well. Another hypoxic gene ATF1 showed similar results.

G. Sequence Specificity of the LORE Binding Activity

To further define the sequence requirements in LORE, a series of single base pair substitutions were made in the site and assayed in vitro. Many of the mutant LOREs had altered DNA-binding ability. These effects varied from the absence of a detectable specific complex formation, B1, for mutant C337A, to a reduction for mutant A346C, to about the same as the wild type LORE for mutant G347T, to an increase in DNA binding for mutant T331G. Another group of mutant LOREs (e.g. A336C and A335C) demonstrated altered complex formation with reduction of B1 but also creation of new shifted bands, suggesting that a new protein-DNA complex may have been created. Substitutions that showed large decreases in specific binding complex formation are concentrated in the center of the LORE. DNA binding was sensitive to single nucleotide substitutions examined between −343 and −335. Therefore, this nonameric sequence (ACTCAACAA, SEQ ID NO: 1) was designated as the DNA binding core of the LORE.

H. Identification of a Family of Genes Under Similar LORE Control

A search of the *S. cerevisiae* genome for LORE core sequences present in the promoter regions of other genes was carried out using DNA Pattern (van Helden, et al., *J. Mol. Biol.* 281:827–842 (1998)) and PatMatch (Cherry, et al.,. "Saccharomyces Genome Database http://genome-www.stanford.edu/Saccharomyces/) web-based tools and the putative LOREs in the promoter region of several genes were aligned (FIG. 1). Some of the potential LOREs (from the promoter sequences of TRX2, FKH1, FTR1, RPL35A and MET22) were found to have exactly the same nine core nucleotides. The potential LOREs from the ATF1 and TIR1 promoter regions each have one nucleotide mismatch in the core region and another potential LORE from SUT1 possesses two mismatches in this region. It is worth noting that the expression of ATF1, TIR1 and SUT1 has been reported to be increased at low oxygen tensions (Bourot, S., et al., *Gene* 165:97–102 (1995); Donzeau, et al., *Mol. Microbiol.* 20:449–459 (1996); Fujimori, et al., *FEBS Lett.* 413:226–230 (1997); Kitagaki, et al., *Eur. J. Biochem.* 249:343–349 (1997)). The hypoxia-induced complex formation of all potential LOREs from the listed genes was tested in vitro using EMSAs. The results demonstrated that, like the wild type LORE from the OLE1 promoter, a hypoxia-induced complex is formed with the putative LOREs from the promoters of the genes. The finding that potential LOREs from RPL35A, TRX2 and MET22 share the same core sequence but exhibit varied degrees of complex formation ability based on the intensity of the B1 band shift implies that the nucleotides outside the core also play an important role in DNA binding. On the other hand, the potential LOREs from ATF1, TIR1, FTR1 and SUT1 with one or two nucleotide mismatches still showed hypoxia-induced DNA binding (even increased DNA binding in the case of ATF1), suggesting that certain positions in the core sequence may be varied yet still function as a LORE in vitro.

To test the possibility that these genes may be hypoxia-inducible, Northern blot analyses of certain genes (ATF1, TRX2, SUT1, FTR1, RPL35A) were performed. Consistent with previous data (Fujiwara, et al., *Yeast* 15:1183–1197 (1999)), ATF1 expression was significantly induced under the hypoxic conditions employed. This study showed for the first time that ATF1 and TRX2 are induced by cobalt treatment as well, similar to OLE1. About a 3 fold hypoxia and 2.5 fold cobalt induction of TRX2 mRNA was observed. The hypoxia-induced SUT1 expression was confirmed; however, there was no significant induction by cobalt. FTR1 mRNA was also examined and it was confirmed that its level was decreased under hypoxic conditions, consistent with previous studies (Hassett, et al., *J. Biol. Chem.* 273:7628–7636 (1998)). RPL35A mRNA level was not changed under hypoxic conditions.

I. RAP1p and LORE Binding Protein(s) (LBP)

RAP1p is a yeast multifunctional protein involved in transcriptional activation/repression, and telomere function. Previous studies on the regulation of the ATF1 gene identified an 18-bp element essential for transcriptional activation in vivo (Fujiwara, et al., *Yeast* 15:1183–1197 (1999)). This element also contains a putative LORE. A purified glutathione S-transferase (GST)-RAP1p fusion was utilized for in vitro EMSA using a probe from the ATF1 promoter containing the 18-bp element. The results showed that RAP1p could form a complex with the ATF1 promoter DNA sequence. To test the possibility of RAP1p involvement in binding to the LORE, EMSAs were performed. The results demonstrated that the putative LORE from ATF1 forms a complex (B1) with the crude extracts from hypoxia treated yeast cells analogous to the LORE from OLE1. On the other hand, a constitutive, strong binding band (B3) was observed using the RAP1p binding sequence from the PGK1 promoter as a probe. Additional EMSAs were performed using a very well characterized RAP1p binding sequence and mutants from the TP1 promoter as probes (Scott, et al., *Mol. Cell. Biol.* 13:543–550 (1993)). These results confirmed that the B3 complex binds RAP1p. A series of EMSAs were done to investigate the relationship between B3 and B1. Unlabeled LORE from either ATF1 or OLE1 could not compete out the B3 and vice versa, suggesting that the constitutive B3 complex involved with RAP1p binding is different from the hypoxia-induced B1 complex involving the LORE from ATF1 and OLE1. Unlabeled LORE of ATF1 could effectively compete out the complex formed with radiolabeled OLE1 LORE and vice versa, which together with the previous B3 competition EMSA results suggest that the complex formed with the OLE1 LORE and the ATF1 LORE are similar. Because there is only one base pair difference in the core region of the LORE between OLE1 and ATF1, a mutated LORE T341C from OLE1 which corresponds to the putative ATF1 LORE was examined. This single base change caused a constitutive complex formation in crude extracts from normoxia and hypoxia. The subsequent cold probe competition EMSAs suggested that that complex was the same as the B3 complex formed by the RAP1p binding sequence from PGK1. The B1 complex could still be observed using hypoxic crude extract, and could be displaced by unlabeled OLE1 LORE probe. In summary, these in vitro results support the hypothesis that the putative LORE of ATF1 functions like the LORE of OLE1 in the regulation of gene expression by hypoxia. Moreover, these data do not support a role for RAP1p binding to the LORE sequence during hypoxic induction.

III. Discussion

OLE1 encodes the Δ-9 fatty acid desaturase, an enzyme involved in the formation of unsaturated fatty acids. This enzyme introduces a double bond between carbons 9 and 10 of substrate palmitoyl (16:0) or stearoyl (18:0)-CoA with molecular $O_2$ serving as an electron acceptor to form palmitoleic (16:1) or oleic (18:1) acid, respectively. Previous studies have demonstrated that OLE1 is upregulated under hypoxic conditions. Its induction under hypoxic conditions may be in response to the limitation of $O_2$ as a substrate.

The experiments discussed herein have confirmed previous data showing that the expression of OLE1 mRNA is increased in hypoxia and in the presence of the transition metals cobalt and nickel under aerobic conditions. The experiments have shown that these stimuli induce an OLE1 promoter-lacZ reporter gene as well. Aerobic incubation with the iron chelator 1,10-Ph also leads to increased OLE1 expression as evidenced by Northern blot and reporter assays. Subsequently, using reporter gene assays and EMSAs, a low oxygen response element (LORE), which functions as a transcriptional activation cis element, was identified. The LORE, about 20 base pairs in length, is necessary and sufficient for OLE1 hypoxia-induced gene expression and is also sufficient for hypoxia-induced gene expression when placed upstream of a heterologous promoter. Further studies demonstrated that the same LORE sequence is involved in OLE1 repression by UFA in normoxic, hypoxic, and cobalt containing conditions. A family of genes containing a similar LORE in their promoter regions was identified by searching the *S. cerevisiae* genome using the nine nucleotide DNA core binding sequence (ACTCAACAA, SEQ ID NO: 1), which was determined by performing EMSAs using a series of single nucleotide substitutions in the OLE1 LORE in vitro. Among them, ATF1, TRX2, SUT1 and TIR1 may be under similar LORE control for hypoxia-inducible gene expression.

Extensive studies over the past decade have defined the transcriptional repression mechanism for the regulation of anoxia-inducible genes in *S. cerevisiae*. This mechanism is illustrated by the regulation of ANB1, a prototypic anaerobic-induced yeast gene. Both genetic and biochemical evidence have demonstrated that the normoxic repression of this gene is mediated by the ROX1p repressor through its binding to the ANB1 operator site. The full repression by ROX1p requires two general transcription mediators, SSN6p and TUP1p. In an anaerobic environment, ROX1 expression is decreased, ROX1p levels decline, and eventually the repression of anoxia regulated genes is released. Heme and Hap1 are involved in ROX1 expression in normoxic conditions. Based on the consensus binding sequence of ROX1p, putative ROX1p binding sequences in the promoter regions of many other genes in *S. cerevisiae*, including OLE1, have been identified. The OLE1 promoter region contains three putative ROX1p binding sites at −130, −260 and −272 relative to the first nucleotide of the translation start codon (Deckert, et al., *Genetics* 150:1429–1441 (1998); Stukey, et al., *J. Biol. Chem.* 265:20144–20149 (1990); Zitomer, et al., *Methods* 11:279–288 (1997)). Previous studies suggested that OLE1 is only slightly derepressed in a ROX1 disruptant under aerobic conditions. The results of the present study confirm that ROX1 does not play a significant role in the basal aerobic expression of the OLE1 gene. There were no significant changes in either reporter gene or OLE1 mRNA expression in a *S. cerevisiae* strain in which the ROX1 gene had been disrupted. Moreover, both hypoxia and cobalt-induced OLE1 gene expression was observed in this strain; the expression of the ROX1 mediated anaerobic yeast gene ANB1 was not upregulated by cobalt.

Multiple pathways involved in regulating hypoxic and anoxic gene expression in yeast may exist (Poyton, *Respir. Physiol.* 115:119–133 (1999)). Studies of several other hypoxic/anaerobic genes including SUT1 (Bourot, S., et al., *Gene* 165:97–102 (1995)), GPD2 (Ansell, et al., *EMBO J.* 16:2179–2187 (1997)), PAU (Rachidi, et al., *Mol. Microbiol.* 35:1421–1430 (2000)) and DAN1 (Sertil, et al., *Gene* 192:199–205 (1997)) have demonstrated ROX1p-independent hypoxic/anaerobic induction. Another hypoxic/anaerobic gene, TIR/SRP1, has variably been reported to be ROX1p-independent and ROX1p-dependent (Donzeau, et al., *Mol. Microbiol.* 20:449–459 (1996); Kitagaki, et al., *Eur. J. Biochem.* 249:343–349 (1997)). The identification of a LORE herein indicates that transcription activation is crucial to the increased expression of certain yeast genes in response to extremely low oxygen tension (vs. complete anaerobiosis).

OLE1 appears to be induced maximally by hypoxia as opposed to anoxia; a genome-wide transcriptional analysis of aerobic and anaerobic chemostat cultures of *S. cerevisiae* demonstrated that OLE1 has only a marginal (1.3 fold) increase under stringent anaerobic conditions. Thus, OLE1 represents a yeast gene that is regulated by hypoxia, certain transition metals and iron chelation, strikingly similar to several hypoxia-inducible mammalian genes, such as Epo, VEGF, the glucose transporters GLUT1 and GLUT3, and several glycolytic enzymes. Given the importance of the ability to adapt to hypoxic stress throughout evolution, it is not surprising to find yeast and mammalian genes which are similarly regulated. Studies of several hypoxia-inducible mammalian genes have led to the identification of a hypoxia responsive element (HRE) (Beck, et al., *J. Biol. Chem.* 266:15563–15566 (1991); Blanchard, et al., *Mol. Cell. Biol.* 12:5373–5385 (1992); Pugh, et al., *Proc. Natl Acad. Sci. USA* 8:1053–10557 (1991); Semenza, et al., *Proc. Natl Acad. Sci. USA* 88:5680–5684 (1991)) and the heterodimeric hypoxia-inducible factor HIF-1 which binds to it (Wang, et al., *J. Biol. Chem.* 270:1230–1237 (1995)). Although functionally the LORE and HRE are similar, sequence analysis does not reveal any similarity.

TABLE 1

Oligonucleotides used in this study

| Name | Sequence[a] | | | | |
|---|---|---|---|---|---|
| Oligonucleotides for EMSA (LORE identification) | | | | | |
| 1-5' | −397− | AACGGCTTAAGGTTCTCTT − | −378 | SEQ ID NO:30 |
| 1-3' | −378− | AAGAGAACCTTAAGCCGTT − | −397 | SEQ ID NO:31 |
| 2-5' | −377− | CGCATAGTCGGCAGCTTTCT − | −358 | SEQ ID NO:32 |
| 2-3' | −358− | AGAAAGCTGCCGACTATGCG− | −377 | SEQ ID NO:33 |
| 3-5' | −357− | TTCGGACGTTGAACACTCAA − | −338 | SEQ ID NO:34 |
| 3-3' | −338− | TTGAGTGTTCAACGTCCGAA − | −357 | SEQ ID NO:35 |
| 4-5' | −337− | CAAACCTTATCTAGTGCCCCA− | −318 | SEQ ID NO:36 |

TABLE 1-continued

Oligonucleotides used in this study

| Name | Sequence[a] | | | |
|---|---|---|---|---|
| 4-3' | -318- | TGGGCACTAGATAAGGTTTG - | -337 | SEQ ID NO:37 |
| 5-5' | -317- | ACCAGGTGTGCTTTCTACGAG - | -298 | SEQ ID NO:38 |
| 5-3' | -298- | CTCGTAGAAGCACACCTGGT - | -317 | SEQ ID NO:39 |
| 6-5' | -297- | TCTTGCTCACTCAGACACAC - | -278 | SEQ ID NO:40 |
| 6-3' | -278- | GTGTGTCTGAGTGAGCAAGA - | -297 | SEQ ID NO:41 |
| 7-5' | -277- | CTATCCCTATTGTTACGGCTAT - | --256 | SEQ ID NO:42 |
| 7-3' | -256- | ATAGCCGTAACAATAGGGATAG- | -277 | SEQ ID NO:43 |
| 8-5' | -387- | AGGTTCTCTTCGCATAGTCG - | -368 | SEQ ID NO:44 |
| 8-3' | -368- | CGACTATGCGAAGAGAACCT- | -387 | SEQ ID NO:45 |
| 9-5' | -367- | GCAGCTTTCTTTCGGACGTT - | -348 | SEQ ID NO:46 |
| 9-3' | -348- | AACGTCCGAAAGAAAGCTGC- | -367 | SEQ ID NO:47 |
| 10-5' | -347- | GAACACTCAACAAACCTTAT - | -328 | SEQ ID NO:3 |
| 10-3' | -328- | ATAAGGTTTGTTGAGTGTTC - | -347 | SEQ ID NO:48 |
| 11-5' | -327- | CTAGTGCCCAACCAGGTGTG - | -308 | SEQ ID NO:49 |
| 11-3' | -308- | CACACCTGGTTGGGCACTAG - | -327 | SEQ ID NO:50 |
| 12-5' | -307- | CTTCTACGAGTCTTGCTCAC - | -288 | SEQ ID NO:51 |
| 12-3' | -288- | GTGAGCAAGACTCGTAGAAG- | -307 | SEQ ID NO:52 |
| 13-5' | -287- | TCAGACACACCTATCCCTAT - | -268 | SEQ ID NO:53 |
| 13-3' | -268- | ATAGGGATAGGTGTGCTGA - | -287 | SEQ ID NO:54 |
| 14-5' | -267- | TGTTACGGCTAT | - | -256 | SEQ ID NO:55 |
| 14-3' | -256- | ATAGCCGTAACA | - | -267 | SEQ ID NO:56 |

Oligonucleotides for plasmid construction

| Name | | Sequence | | |
|---|---|---|---|---|
| LacZ-3' | | CCATTCAGGCTGCGCAA 35 SEQ ID NO.57 | | |
| yd-8 | | GCTTTCTTTCG*AAGCTT*AACGGCTTAA[b] SEQ ID NO.58 | | |
| yd-10 | -234- | TCCACCTTTGTGTGCCATC - | -252 | SEQ ID NO.59 |
| yd-19 | -347- | GAACAtaCgACAAACCTTAT - | -328[c] | SEQ ID NO.60 |
| yd-20 | -328- | ATAAGGTTTGTcGtaTGTTC - | -347 | SEQ ID NO.61 |

[a]Numbers at 5' and 3' ends of oligonucleotides indicate the position of the nucleotide of OLE1 promoter with respect to the start codon (A of ATG is +1).
[b]Underlined indicates the restriction site
[c]Small case letter indicates mutation in sequence

TABLE 2

Yeast (S. cerevisiae) strains and plasmids

| Strains and Plasmids | Genotype | Plasmid | Source |
|---|---|---|---|
| RZ53-6 | a trpl-289, leu2-3, 112, Ura3-52, adel-100 | | R. Zitomer |
| | | [p62::934] | Numbers following :: indicate the position of the nucleotide at the 5' end of the OLE1 promoter fragment with |
| | | [p62::856] | |
| | | [p62::792] | |
| | | [p62::576] | |

This study

TABLE 2-continued

Yeast (*S. cerevisiae*) strains and plasmids

| Strains and Plasmids | Genotype | Plasmid | Source |
|---|---|---|---|
| [p62::488] [p62::471] [p62::396] [p62::255] | | respect to the start codon (A of ATG is +1) in lacZ fusion constructs (Choi et al. 1996). | |
| [pAM4] | | The OLE1 promoter contains-C342T[a],-T341A and -A339G mutations in p62::934 | This study |
| [pTBA30] | | Basal CYC1 promoter-lacZ fusion | This study |
| [pAM6] | | A tandem (+) repeat LORE-basal CYC1 promoter-lacZ | This study |
| [pAM7] | | (−) LORE-basal CYC1 promoter-lacZ fusion | This study |
| [pAM10] | | (+) mutant LORE-basal CYC1 promoter-lacZ fusion | This study |
| [pAM16] | | (+) LORE-basal CYC1 promoter-lacZ fusion | This study |
| RZ53-6Δrox1 | a trpl-289, leu2-3, 112, Ura3-52, adel-100, rox1::leu2 | | R. Zitomer |
| [p62::934] | | | This study |

[a]Numbers indicate the position of the nucleotide of OLE1 promoter with respect to the start codon (A of ATG is +1); the letter in front of the number represents the wild type nucleotide and the letter after the number is the nucleotide substituted.

All references cited herein are fully incorporated by reference. Having now fully described the invention, it will be understood by one of skill in the art that the invention may be performed within a wide and equivalent range of conditions, parameters and the like, without affecting the spirit or scope of the invention or any embodiment thereof.

What is claimed is:

1. A vector for recombinantly expressing a peptide or protein in a eukaryotic cell, comprising:
   (a) a promoter which is active in yeast;
   (b) a hypoxia responsive enhancer element consisting essentially of a nucleotide sequence selected from the group consisting: SEQ ID NO: 1; and SEQ ID NO:2; and
   (c) a DNA sequence encoding said peptide or protein, wherein said DNA sequence:
      (i) is operably linked to said promoter; and
      (ii) is non-homologous to said hypoxia responsive enhancer element.

2. The vector of claim 1, wherein said promoter is the CYC1 basal promoter.

3. The vector of claim 1, wherein said peptide or protein is toxic to cancer cells.

4. A vector for recombinantly expressing in a eukaryotic cell a protein or peptide toxic to cancer cells, comprising:
   (a) a promoter which is active in said eukaryotic cell;
   (b) a hypoxia responsive enhancer element consisting essentially of a (nucleotide sequence selected from the group consisting of: SEQ ID NO: 1; and SEQ ID NO:2; and
   (c) a DNA sequence encoding said peptide or protein toxic to cancer cells, wherein said DNA sequence:
      (i) is operably linked to said promoter; and
      (ii) is non-homologous to said hypoxia responsive enhancer element.

5. A host cell transformed with the vector of any one of claims 1–4.

6. The host cell of claim 5, wherein said host cell is a yeast.

7. A method for recombinantly producing a peptide or protein in a eukaryotic cell, comprising:
   (a) growing host cells transformed with a vector under anaerobic conditions, wherein said vector comprises:
      (i) a promoter that is active in said eukaryotic cell;
      (ii) a hypoxia responsive enhancer element consisting essentially of a nucleotide sequence selected from the group consisting of: SEQ ID NO:1; and SEQ ID NO:2; and
      (iii) a DNA sequence encoding said peptide or protein, wherein said DNA sequence:
         (A) is operably linked to said promoter; and
         (B) is non-homologous to said hypoxia responsive element;
   (b) purifying said recombinant peptide or protein from either said host cells or from the medium surrounding said host cells.

8. The method of claim 7, wherein said promoter is active in yeast.

9. The method of claim 8, wherein said promoter is the CYC1 promoter.

10. The method of claim 7, wherein said host cells are yeast.

11. The method of any one of claims 7–10, further comprising exposing the transformed host cells to an agent that induces recombinant gene expression, wherein said agent is selected from the group consisting of: a transition metal; and an iron chelator.

12. The method claim 11, wherein said agent is selected from the group consisting of: cobalt; and nickel.

13. A method for recombinantly producing a peptide or protein in a eukaryotic cell, comprising:
   (a) growing host cells transformed with a vector under aerobic conditions, wherein said vector comprises:
      (i) a promoter that is active in said eukaryotic cell;
      (ii) a hypoxia responsive enhancer element consisting essentially of a nucleotide sequence selected from the group consisting of: SEQ ID NO:1; and SEQ ID NO:2; and
      (iii) a DNA sequence encoding said peptide or protein, wherein said DNA sequence:

(A) is operably linked to said promoter; and
(B) is non-homologous to said hypoxia responsive element;

(b) inducing recombinant expression of said peptide or protein by exposing said host cells to anaerobic conditions; and (c) purifying said recombinant peptide or protein from either said host cells or from the medium surrounding said host cells.

14. The method of claim 13, wherein said promoter is active in yeast.

15. The method of claim 14, wherein said promoter is the CYC1 promoter.

16. The method of any one of claims 13–15, wherein said host cells are yeast.

17. A method for recombinantly producing a peptide or protein in a eukaryotic cell, comprising:
(a) growing host cells transformed with a vector under aerobic conditions, wherein said vector comprises.
  (i) a promoter that is active in said eukaryotic cell;
  (ii) a hypoxia responsive enhancer element consisting essentially of a nucleotide sequence selected from the group consisting of: SEQ ID NO:1; and SEQ ID NO:2; and
  (iii) a DNA sequence encoding said peptide or protein, wherein said DNA sequence:
    (A) is operably linked to said promoter; and
    (B) is non-homologous to said hypoxia responsive element;

(b) inducing recombinant gene expression by exposing said host cells to either a transition metal or an iron chelator; and (c) purifying said recombinant peptide or protein from either said host cells or from the medium surrounding said host cells.

18. The method of claim 17, wherein said promoter is active in yeast cells.

19. The method of claim 18, wherein said promoter is the CYC1 promoter.

20. The method of claim 17, wherein said host cells are yeast.

21. The method of any one of claims 17–20, wherein said agent is a transition metal selected from the group consisting of: cobalt and nickel.

* * * * *